US008386062B2

(12) United States Patent
Yau et al.

(10) Patent No.: US 8,386,062 B2
(45) Date of Patent: Feb. 26, 2013

(54) METHOD OF PREPARING DIGITAL MODEL AND ARTIFICIAL TOOTH APPLIED TO DENTAL IMPLANT

(75) Inventors: Hong-Tzong Yau, Chiayi County (TW); Chuan-Chu Kuo, Chiayi County (TW); Jiun-Ren Chen, Yunlin County (TW); Chien-An Chen, Koahsiung County (TW); Lee-Sen Tsou, Hsinchu (TW)

(73) Assignee: Pou Tu Biotechnology Co., Ltd., Chang Hwa Hsien (TW)

( * ) Notice: Subject to any disclaimer, the term of this patent is extended or adjusted under 35 U.S.C. 154(b) by 390 days.

(21) Appl. No.: 12/923,018

(22) Filed: Aug. 30, 2010

(65) Prior Publication Data

US 2011/0123955 A1  May 26, 2011

(30) Foreign Application Priority Data

Nov. 26, 2009 (TW) ................................ 98140424 A

(51) Int. Cl.
*A61C 5/00* (2006.01)
*A61C 5/10* (2006.01)
*A61C 8/00* (2006.01)
*A61C 9/00* (2006.01)
*G06F 19/00* (2011.01)

(52) U.S. Cl. ....... 700/98; 433/201.1; 433/214; 433/215; 433/223

(58) Field of Classification Search ................. 433/223, 433/201.1, 214, 215; 700/98
See application file for complete search history.

(56) References Cited

U.S. PATENT DOCUMENTS

| | | | | |
|---|---|---|---|---|
| 5,273,429 A * | 12/1993 | Rekow et al. | ................. | 433/215 |
| 5,562,450 A * | 10/1996 | Gieloff et al. | ................. | 433/223 |
| 6,293,797 B1 * | 9/2001 | Melot et al. | ................. | 433/202.1 |
| 6,935,862 B2 * | 8/2005 | Harlan | ........................... | 433/218 |
| 7,383,094 B2 * | 6/2008 | Kopelman et al. | ............. | 700/118 |
| 7,493,182 B2 * | 2/2009 | Weber et al. | ..................... | 700/95 |
| 7,555,403 B2 * | 6/2009 | Kopelman et al. | ............ | 702/152 |
| 7,819,662 B2 * | 10/2010 | Marshall et al. | .............. | 433/218 |
| 7,925,374 B2 * | 4/2011 | Andersson et al. | .......... | 700/206 |
| 8,206,152 B2 * | 6/2012 | Holzner et al. | ............... | 433/195 |
| 8,244,390 B2 * | 8/2012 | Kuo et al. | ....................... | 700/98 |
| 2001/0018622 A1 * | 8/2001 | Asano et al. | ..................... | 700/98 |
| 2004/0137408 A1 * | 7/2004 | Embert et al. | ............. | 433/201.1 |
| 2008/0280259 A1 * | 11/2008 | Wen | .............................. | 433/213 |
| 2008/0305458 A1 * | 12/2008 | Lemchen | ..................... | 433/223 |
| 2009/0047629 A1 * | 2/2009 | Kim | ................................ | 433/173 |
| 2009/0104583 A1 * | 4/2009 | Yau et al. | ...................... | 433/213 |
| 2009/0111071 A1 * | 4/2009 | Yau et al. | ...................... | 433/173 |
| 2009/0246736 A1 * | 10/2009 | Holzner et al. | ............. | 433/201.1 |
| 2009/0325127 A1 * | 12/2009 | Kusch et al. | ............... | 433/201.1 |
| 2011/0070562 A1 * | 3/2011 | O'Brien et al. | ............... | 433/223 |
| 2011/0123954 A1 * | 5/2011 | Yau et al. | .................. | 433/201.1 |
| 2012/0010740 A1 * | 1/2012 | Swaelens et al. | ............... | 700/98 |
| 2012/0231421 A1 * | 9/2012 | Boerjes et al. | ................ | 433/223 |

* cited by examiner

*Primary Examiner* — Mohammad Ali
*Assistant Examiner* — Jennifer L Norton
(74) *Attorney, Agent, or Firm* — Bacon & Thomas, PLLC

(57) ABSTRACT

A method of preparing a digital model and an artificial tooth applied to dental implant includes the steps of a) combining a jig into a fixture in a patient's oral cavity and scanning the patient's oral cavity by an oral scanner to acquire a first oral digital data and saving it in a computer; b) operating the computer to select one of digital prostheses from a prosthetic database in the computer, arranging a digital positioning jig to correspond to the jig in the first oral digital data, and then combining the selected digital prosthesis with the first oral digital data to generate a second oral data; c) generating a digital oral model based on the second oral digital data; and d) creating a solid oral model.

15 Claims, 11 Drawing Sheets

METHOD OF PREPARING DIGITAL MODEL AND ARTIFICIAL TOOTH APPLIED TO DENTAL IMPLANT

BACKGROUND OF THE INVENTION

1. Field of the Invention

The present invention relates generally to preparing artificial teeth, and more particularly, to a method of preparing a digital model and an artificial tooth applied to dental implant.

2. Description of the Related Art

When a dental implant surgery is done to a patient, after the patient's osseointegration and wound healing, it is necessary to prepare artificial tooth/teeth to complete the whole course of the surgery. A conventional method of preparing the artificial tooth/teeth is to let the patient bite a mold made of silicon to form an oral bite mold and then an oral model is produced based on the oral bite mold. Next, the oral model is sent to a dental technician for production of the artificial tooth/teeth. In the production of the artificial tooth/teeth, an abutment or a dental bar needs to be finished before a dental crown and a dental plate are prepared. However, such production of the artificial tooth/teeth is very time-consuming because a dentist needs to send the silicon mold or the oral model to the dental technician and then the technician also needs to prepare the abutment or the dental bar before preparing the dental crown and the dental plate.

An oral 3D digital scanner is commercially available for directly scanning the patient's oral cavity to acquire oral digital data, replacing the process of acquiring the patient's bite mold, such that the production time and cost can be saved. However, such scanner can only be applied to the general production of the artificial tooth/teeth other than to the patient treated by the dental implant surgery.

U.S. Pat. No. 7,555,403 disclosed a method for reconstructing data associated with an obscured finish line; the method is based on the obscured finish line to create trimmed virtual models or trimmed physical models.

In the aforesaid patent, the digital model or artificial tooth can be acquired only when the natural dental abutment or artificial abutment is available within the scope that the artificial tooth is to be prepared. If the natural dental abutment or artificial abutment is not available within the scope that the artificial tooth is to be prepared, the scanning can be done only after the artificial abutment is installed. In this way, the process of preparing the artificial tooth becomes complicated and the patient needs many diagnoses to complete the whole course of treatment, thus being very inconvenient.

SUMMARY OF THE INVENTION

The primary objective of the present invention is to provide a method of preparing a digital model and an artificial tooth applied to dental implant.

The foregoing objective of the present invention is attained by the method includes the steps of a) arranging a jig under the condition that a patient's oral cavity has a fixture having a connection interface formed at a top side thereof, the jig having a feature and an abutting interface, the abutting interface being formed at a bottom side of the jig and corresponding to the connection interface, the feature being exposed outside the dental gum and fixture in the patient's oral cavity, the connection interface being combined with the abutting interface to enable the jig to be combined into the fixture; and then scanning the patient's oral cavity by an oral scanner to acquire a first oral digital data and saving it in a computer; b) operating the computer to select one of digital prostheses, each of which overlaps a digital jig having a digital feature corresponding to the feature of the jig, from a prosthetic database in the computer; combining the selected digital prosthesis with the first oral digital data by the overlap of the feature of the digital jig and that of the jig in the first oral data, and then removing the jig and the digital jig from the first oral data to generate a second oral data; c) generating a digital oral model based on the second oral digital data; d) preparing a solid oral model based on the digital oral model, the digital prosthesis being substantialized to become a propositional prosthesis during the preparation of the solid oral model, and then preparing a solid prosthesis based on the digital prosthesis, the solid prosthesis having a joint interface corresponding to the connection interface of the fixture; e) preparing a dental crown on the prepositional prosthesis and then adjusting the dental crown according to the solid oral model; and finally installing the dental crown to the solid prosthesis to complete the artificial tooth.

The method of the present invention further includes alternative steps of c) separating the digital prosthesis from the second oral digital data to enable the digital prosthesis to be exposed out of the abutting interface and enable the second oral digital data to be exposed out of the connection interface, and then generating a digital oral model based on the second oral digital data; d) preparing a solid oral model based on the digital oral model, the digital prosthesis becoming a solid prosthesis, the digital prosthesis having a joint interface, the joint interface corresponding to the connection interface.

DETAILED DESCRIPTION OF PREFERRED EMBODIMENTS

Figure 1:
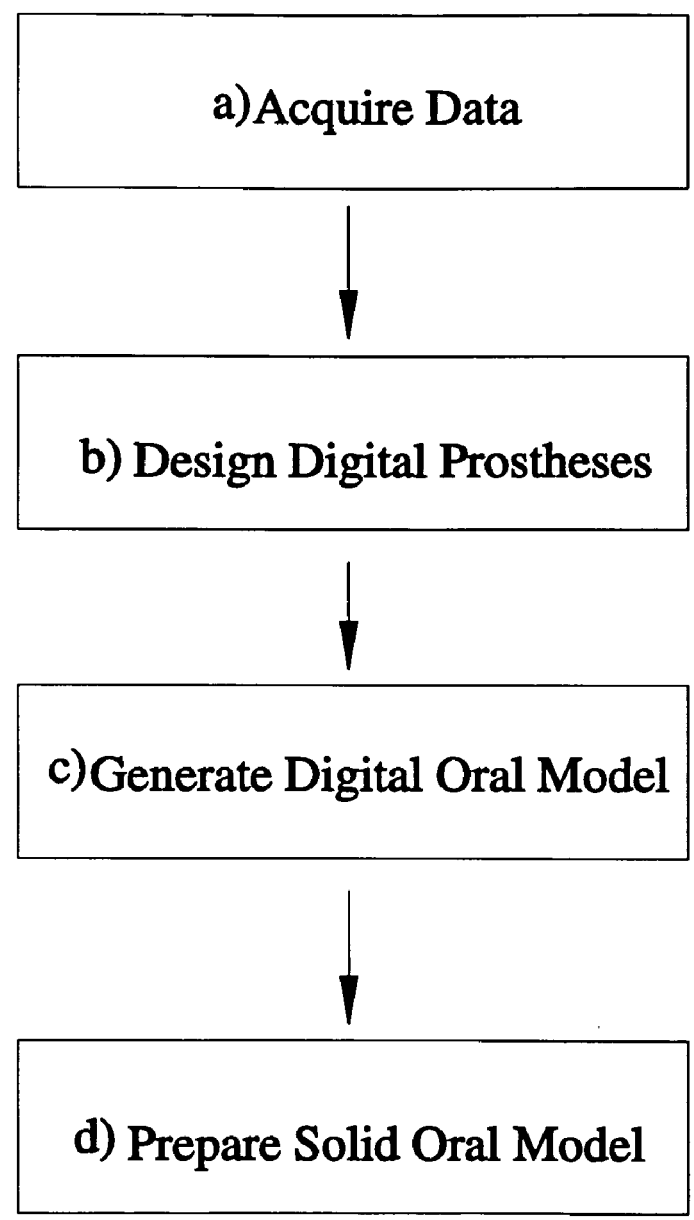
FIG. 1 is a flow chart of a first preferred embodiment of the present invention.
Figure 2:
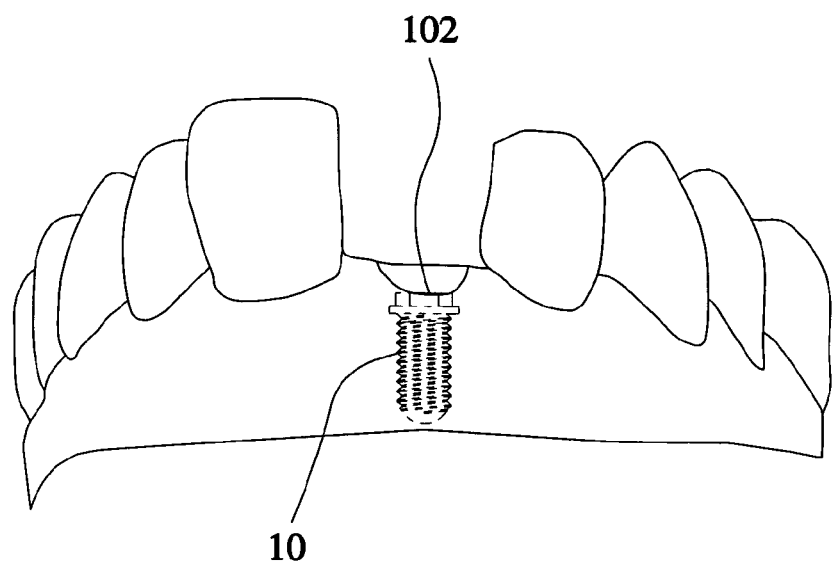
FIG. 2 is a schematic view of the first preferred embodiment of the present invention, showing a part of the patient's oral cavity in which the fixture is located.
Figure 3:
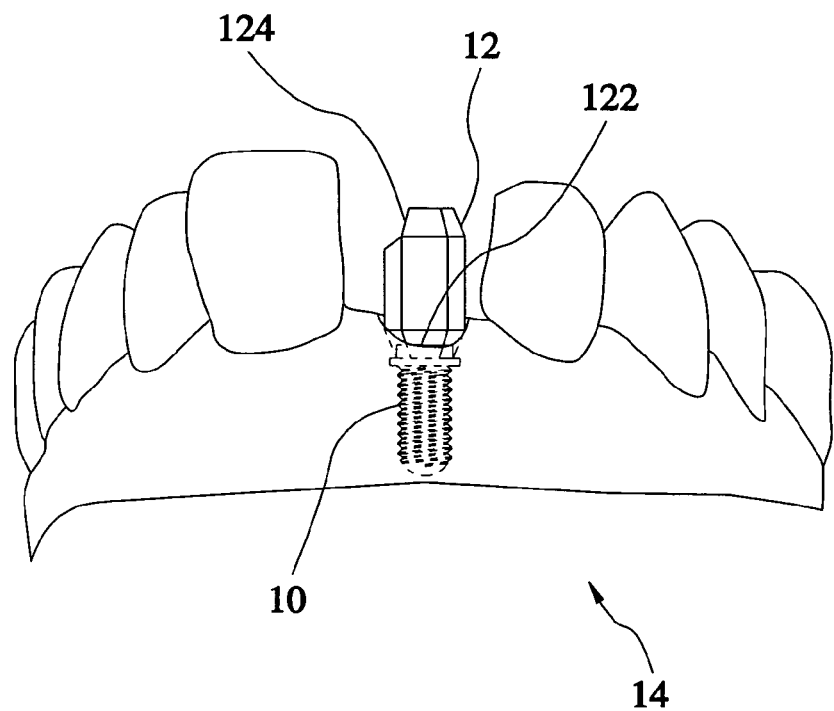
FIG. 3 is another schematic view of the first preferred embodiment of the present invention, showing that the jig is mounted to the fixture.
Figure 4:
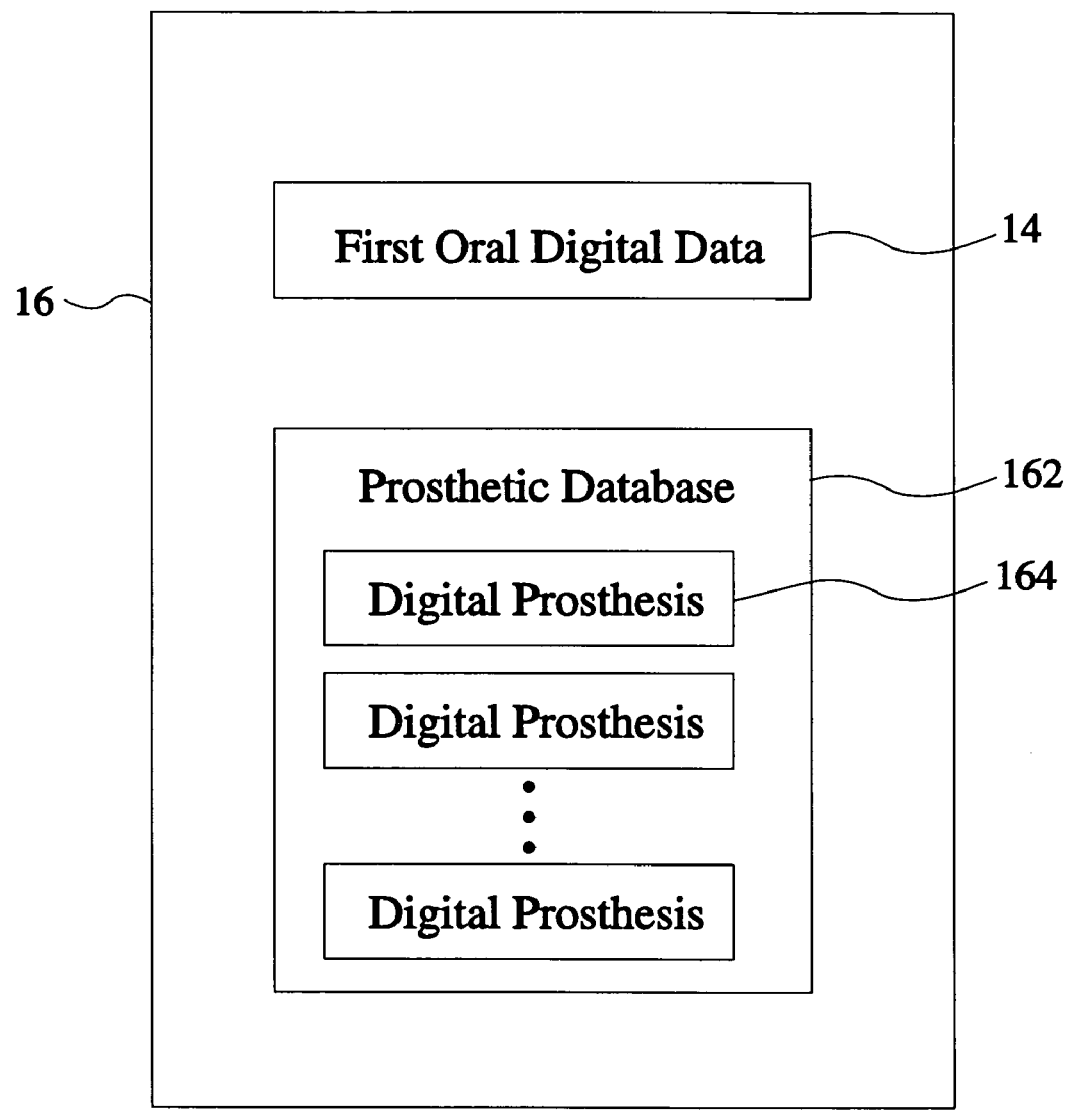
FIG. 4 is another schematic view of the first preferred embodiment of the present invention, showing the data saved in the computer.
Figure 5:
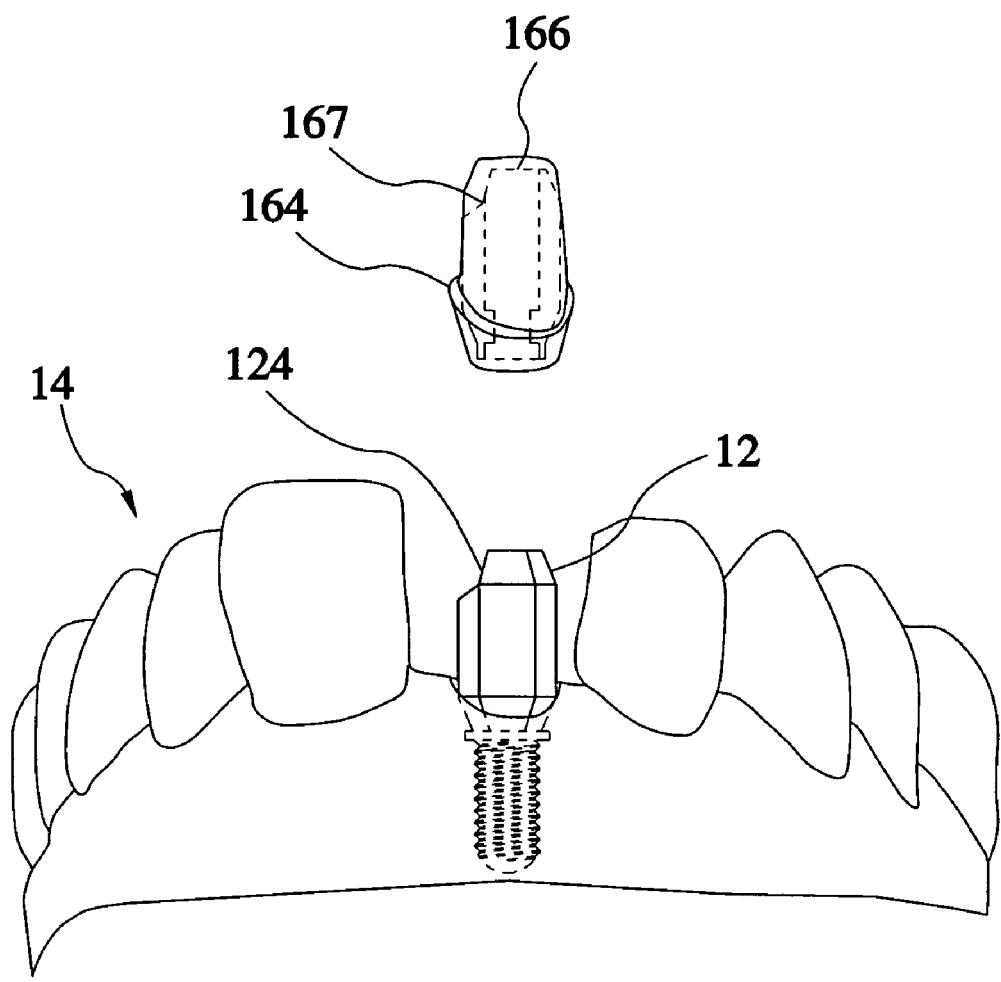
FIG. 5 is another schematic view of the first preferred embodiment of the present invention, showing the digital prosthesis and the digital positioning jig.
Figure 6:
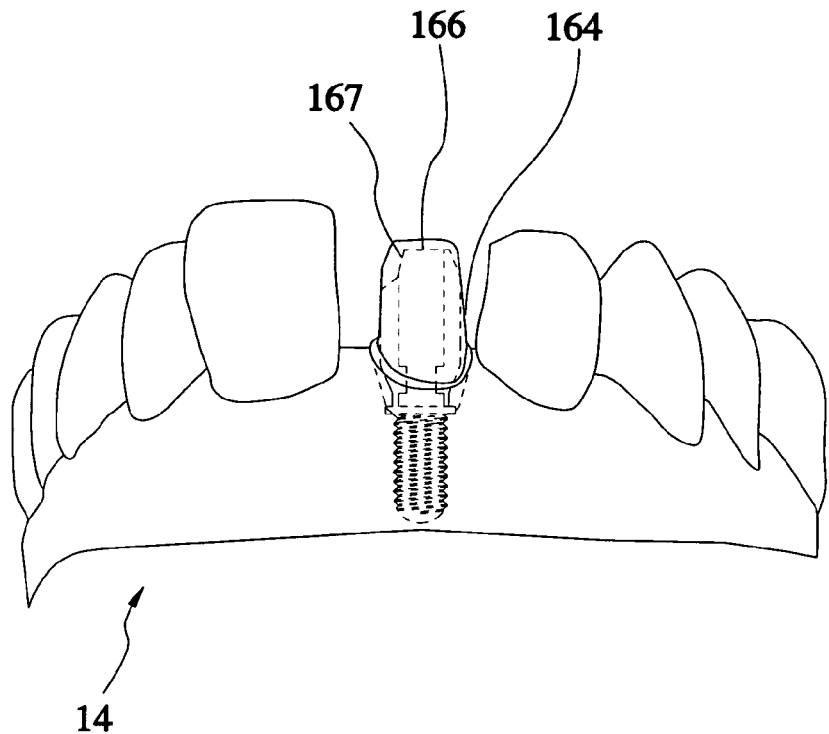
FIG. 6 is another schematic view of the first preferred embodiment of the present invention, showing that the digital prosthesis is combined with the first oral digital data.
Figure 7:
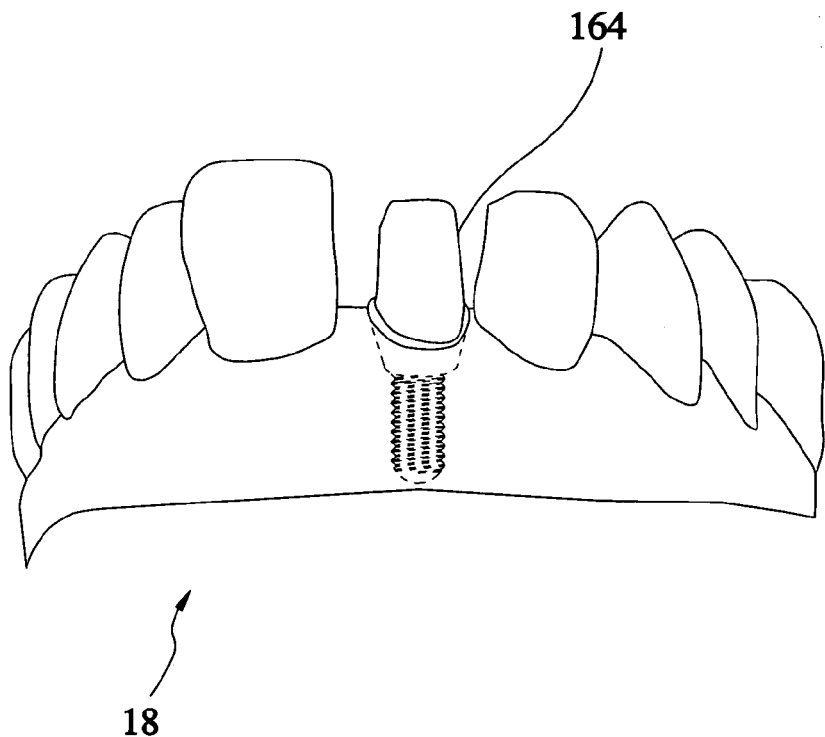
FIG. 7 is another schematic view of the first preferred embodiment of the present invention, showing that the digital prosthesis is combined with the first oral digital data and the jig and the digital positioning jig is removed.
Figure 8:
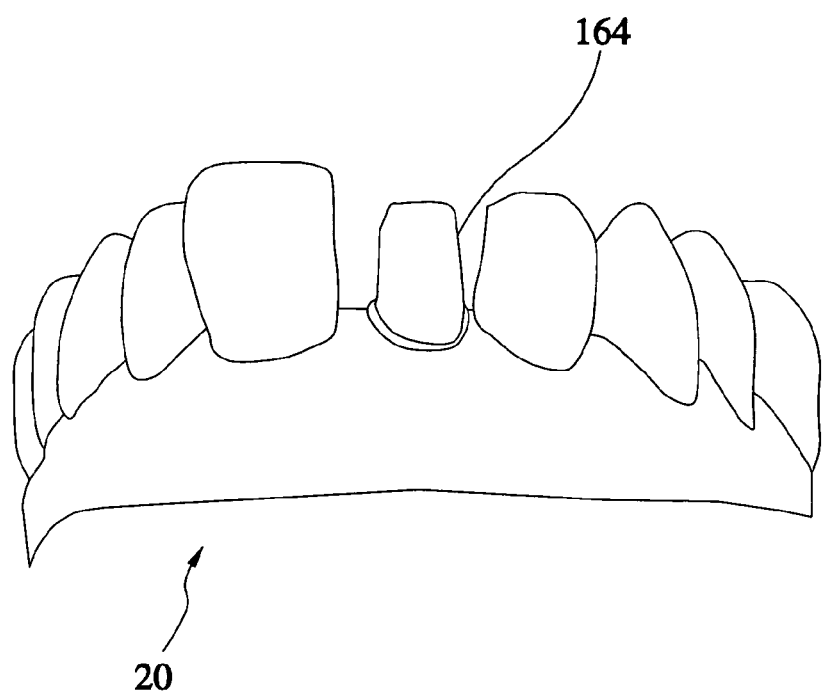
FIG. 8 is another schematic view of the first preferred embodiment of the present invention, showing the digital oral model.
Figure 9:
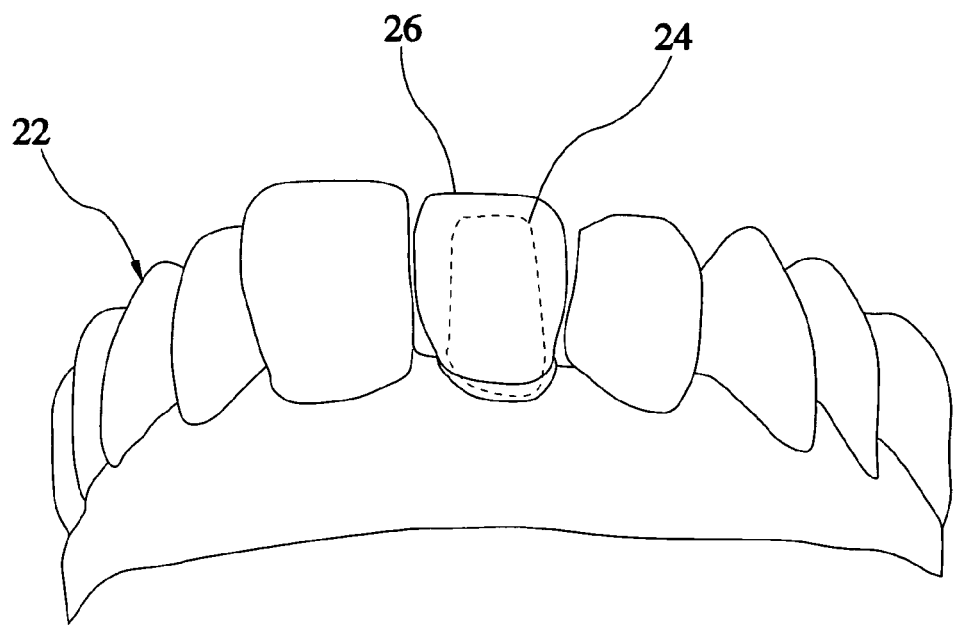
FIG. 9 is another schematic view of the first preferred embodiment of the present invention, showing the solid oral model and the dental crown.
Figure 10:
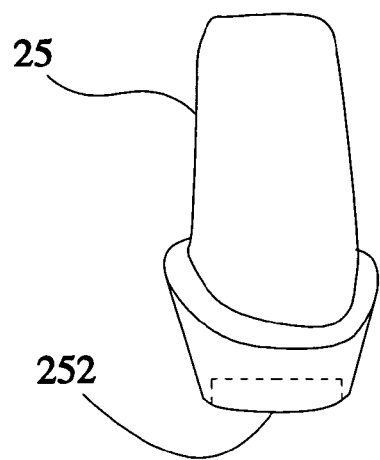
FIG. 10 is another schematic view of the first preferred embodiment of the present invention, showing the solid prosthesis.
Figure 11:
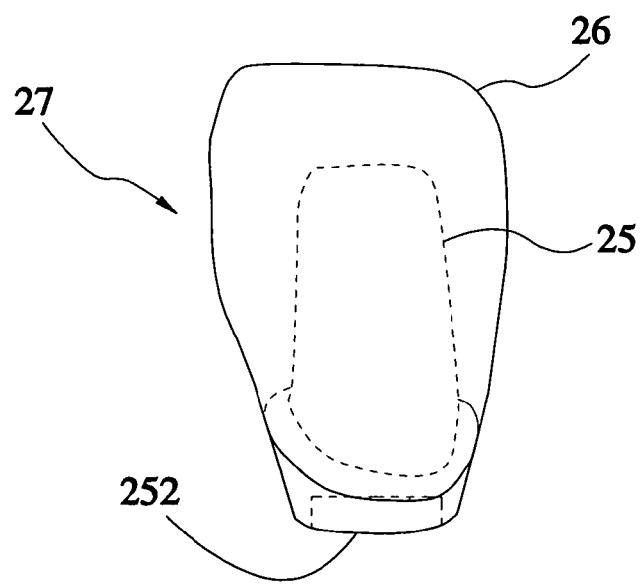
FIG. 11 is another schematic view of the first preferred embodiment of the present invention, showing that the artificial tooth is completed.

Referring to FIG. 1, a method of preparing a digital model and an artificial tooth applied to dental implant in accordance with a first preferred embodiment of the present invention includes the following steps.

a) Referring to FIGS. 2-4, arrange a jig 12 under the condition that a patient's oral cavity has a fixture 10. The fixture 10 includes a connection interface 102 located at a top side thereof. The jig 12 includes an abutting interface 122 and a feature 124. The abutting interface 122 is located at a bottom side of the jig 12 and corresponds to the connection interface 102. The feature 124 is exposed outside the fixture 10 and dental gum in the patient's oral cavity. The abutting interface 122 can be combined with the connection interface 102 in such a way that the jig 12 can be combined into the fixture 10. Next, scan the patient's oral cavity by an oral scanner (not shown) to acquire a first oral digital data 14 and then save it into a computer 16.

b) Referring to FIGS. 4-7, operate the computer 16 to select one of digital prostheses 164, each of which overlaps a digital jig 166 (FIG. 5) having a digital feature 167, from a prosthetic database 162 in the computer 16. Next, combine the selected digital prosthesis 164 and a fixture of the first oral digital data 14, as shown in FIG. 6, by that the digital feature 167 of the digital jig 166 corresponds to the feature 124 of the jig 12 in the first oral digital data 14. After that, remove the jig 12 and the digital jig 166 from the first oral data 14 and the digital prostheses 164 to generate a second oral data 18 (FIG. 7). It is to be noted that the selected digital prosthesis 164 can be a digital precise dental bar or a digital artificial abutment. In this embodiment of the present invention, the selected digital prosthesis 164 is a digital dental bar.

c) Referring to FIG. 8, generate a digital oral model 20 based on the second oral digital data 18. The digital oral model 20 includes the patient's oral shape and the status of the selected digital prosthesis 164 installed in the patient oral cavity.

d) Referring to FIG. 9, prepare a solid oral model 22 based on the digital oral model 20. The selected digital prosthesis 164 is substantialized to become a propositional prosthesis 24. Executing the above steps a) to d) can complete preparation of the digital model of an artificial tooth. If it is intended to prepare the artificial tooth, it will need an addition step as follows.

e) Referring to FIG. 10, prepare a solid prosthesis 25 based on the selected digital prosthesis 164. The solid prosthesis 25 includes a joint interface 252 corresponding to the connection interface 102 of the fixture 10. Referring to FIG. 9 again, prepare a coping and a crown on the prepositional prosthesis 24 to create a dental crown 26. Next, adjust the dental crown 26 according to the solid oral model 22. Finally, remove the dental crown 26 from the prepositional prosthesis 24, referring to FIG. 11, and then install the dental crown 26 to the solid prosthesis 25 to complete an artificial tooth 27. Each of the prepositional prosthesis 24 and the solid prosthesis 25 is made of metal, ceramic, resin or wax, and then processed by a numerical processing machine or casted or both.

Figure 12:
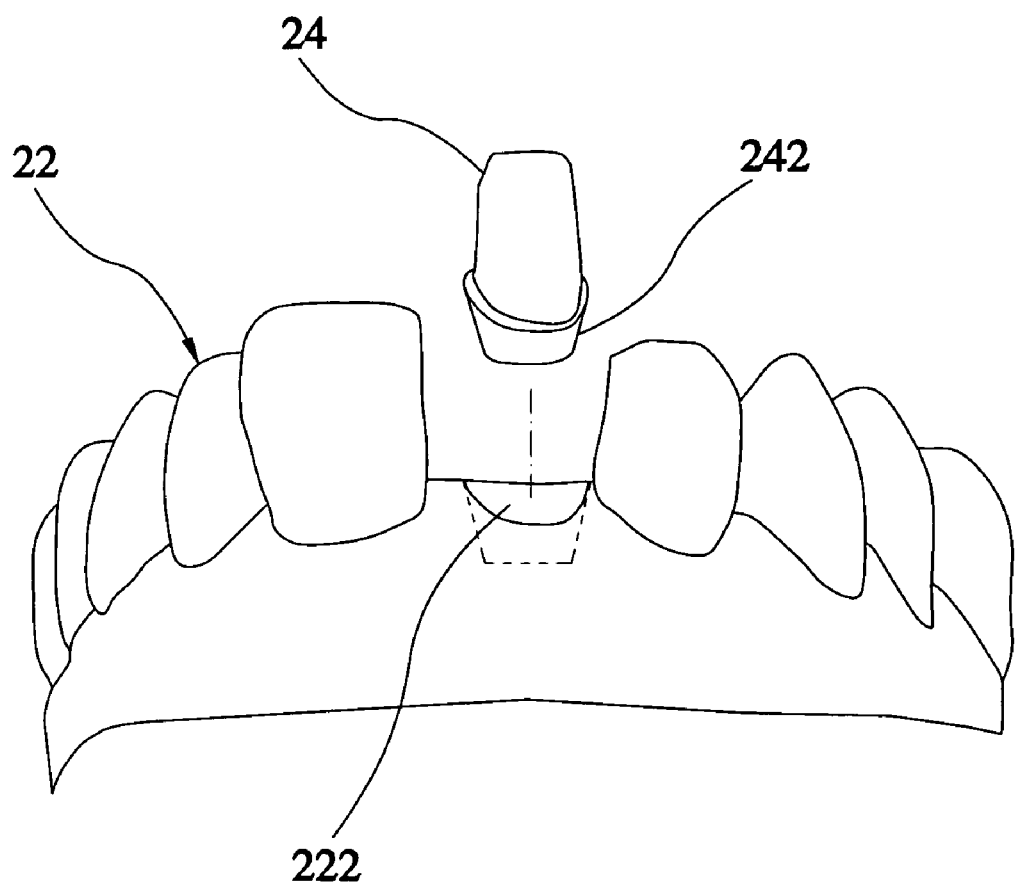
FIG. 12 is another schematic view of the first preferred embodiment of the present invention, showing that the solid oral model has a cavity and the propositional prosthesis has a plug-in portion formed at a bottom side thereof.

Referring to FIG. 12, the prepositional prosthesis 24 can alternatively be independent from the solid oral model 22, and meanwhile, the solid oral model 22 includes a cavity 222. The propositional prosthesis 24 includes a plug-in portion 242 formed at a bottom side thereof and fitting the cavity 222. The plug-in portion 242 is fixedly inserted into the cavity 222 without any movement.

Figure 13:
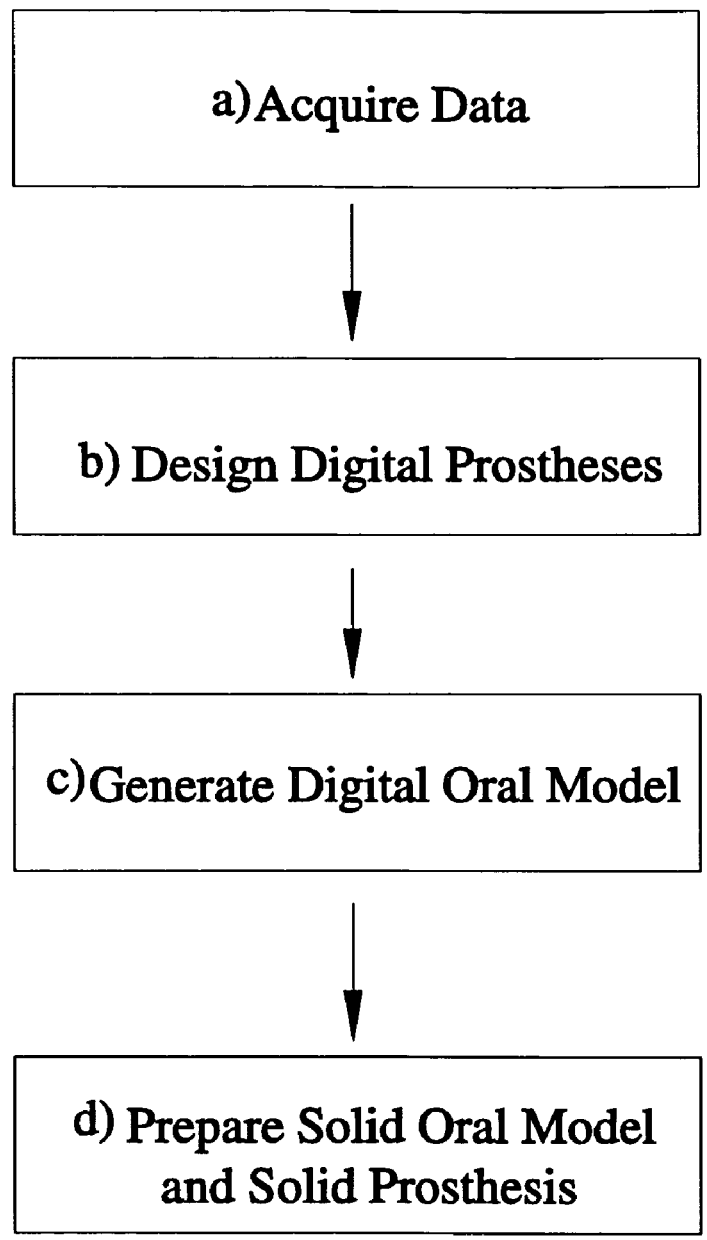
FIG. 13 is a flow chart of a second preferred embodiment of the present invention.
Figure 14:
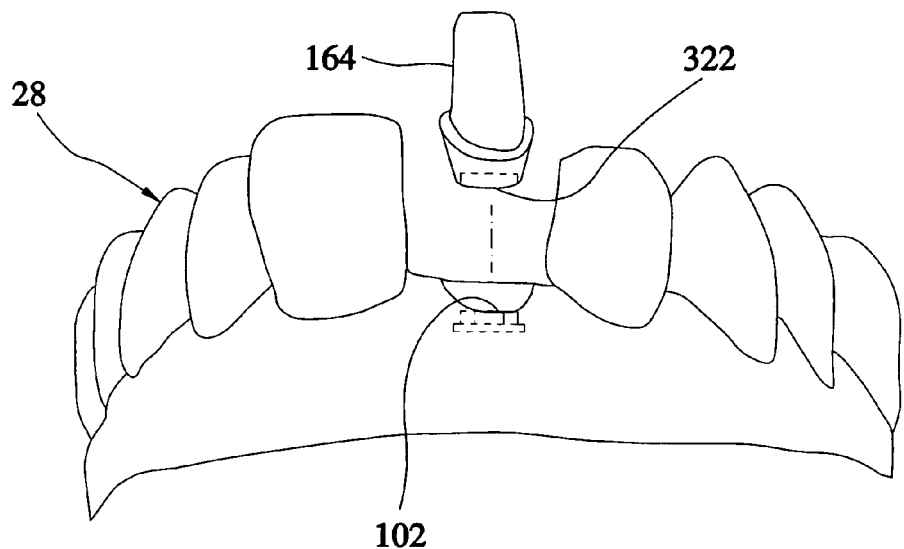
FIG. 14 is a schematic view of the second preferred embodiment of the present invention, showing that the digital prosthesis is separated from the second oral digital data.
Figure 15:
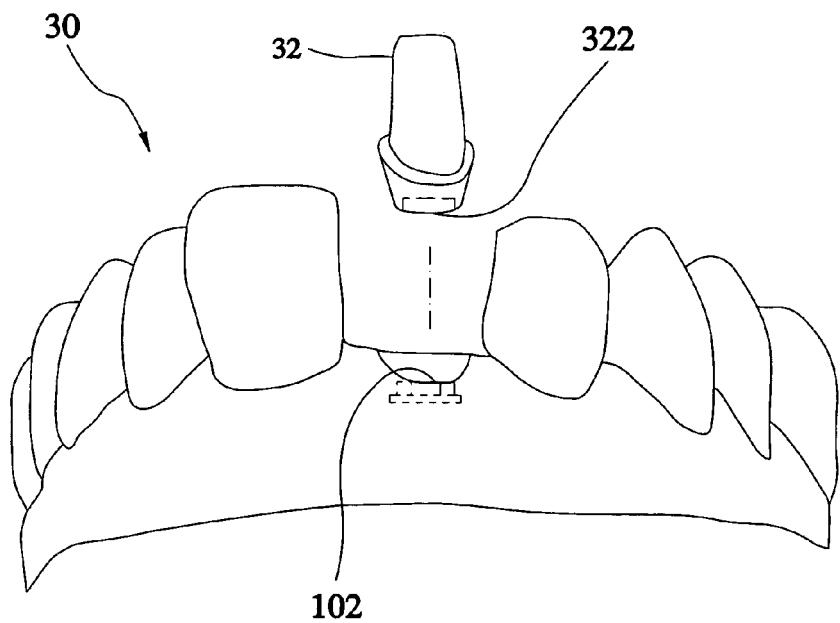
FIG. 15 is another schematic view of the second preferred embodiment of the present invention, showing the solid oral model.

Referring to FIG. 13, a method of preparing an artificial tooth for dental implant in accordance with a second preferred embodiment of the present invention is similar to that of the second embodiment, having the following difference.

c) Referring to FIGS. 14-15, separate the digital prosthesis 164 from the second oral digital data 18 to expose the digital prosthesis 164 out of the abutting interface 122. In the meantime, the second oral digital data 18 is exposed out of the connection interface 102. Next, generate a digital oral model 28 (not shown) based on the second oral digital model 18 after processing.

d) Prepare a solid oral model 30 based on the digital oral model 28 having the connection interface 102. Next, the digital prosthesis 164 can be substantialized into a solid prosthesis 32. The solid prosthesis 32 has a joint interface 322 corresponding to the fixture 10 of the connection interface 102.

Figure 16:
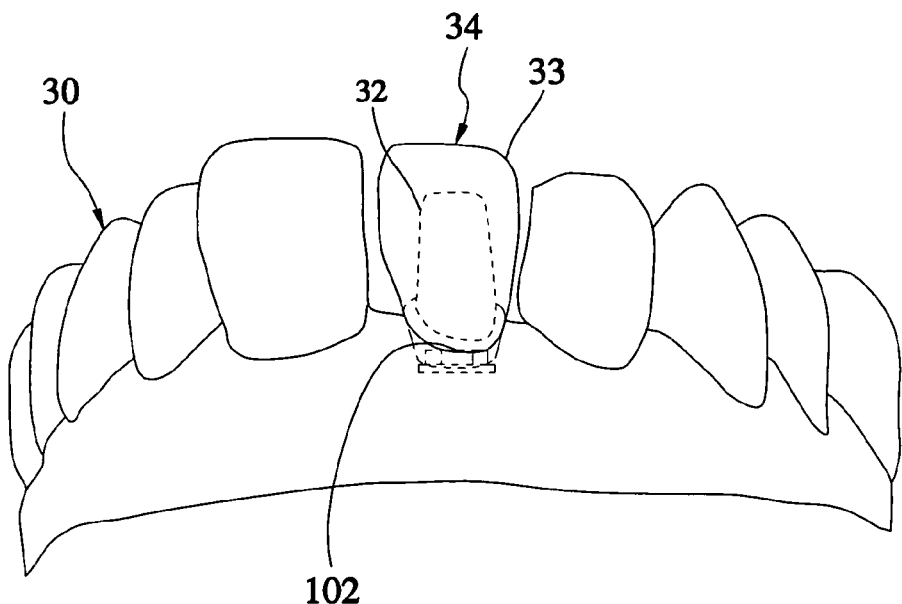
FIG. 16 is another schematic view of the second preferred embodiment of the present invention, showing that the artificial tooth is completed.

In the second embodiment, if it is intended to prepare an artificial tooth, it will need an addition step as follows.

e) Referring to FIG. 16, combine the solid prosthesis 32 into the solid oral model 30 by combination of the connection interface 102 and the joint interface 322 and next directly build up porcelain on the solid prosthesis 32 to complete an artificial tooth 34, and then adjust the artificial tooth 34 according to the solid oral model 30. Alternatively, the dental crown 33 can be created by preparing a coping and a crown on the solid prosthesis 32. Finally, fasten the dental crown 33 to the solid prosthesis 32 to complete the artificial tooth 34. In this embodiment, the solid prosthesis 32 is made of metal, ceramic, resin or wax, and then processed by a numerical processing machine or casted or both.

Figure 17:
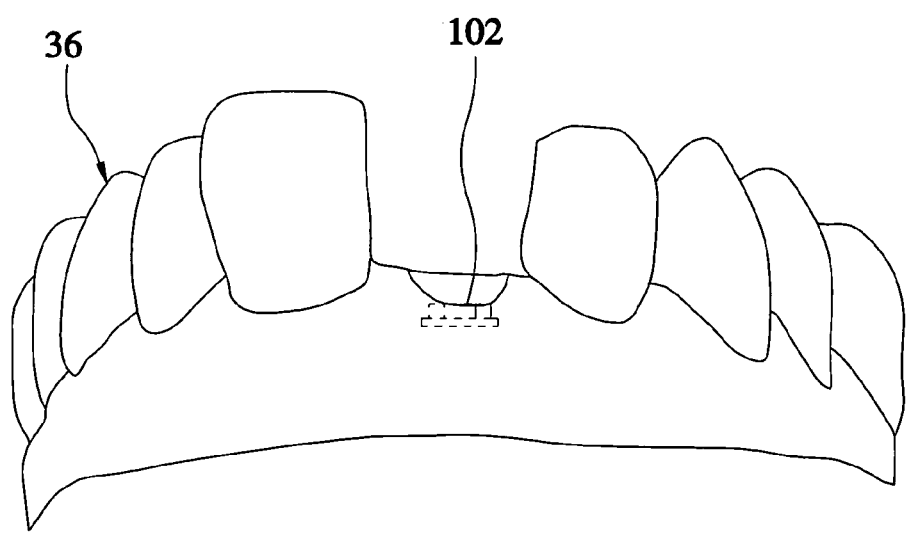
FIG. 17 is another schematic view of the second preferred embodiment of the present invention, showing the third oral digital data.

Referring to FIG. 17, a method of preparing an artificial tooth for dental implant in accordance with a third preferred embodiment of the present invention is similar to that of the second embodiment, having the following difference. In the step a), before the jig 12 is combined into the fixture 10, scan the patient's oral cavity by an oral scanner to acquire a third oral digital data 36 and save it in the computer 16. Compare the connection interface 102 of the third oral digital data 36 with the connection interface 102 of the second oral digital data 18 to confirm the accuracy of the second digital data 18.

It is to be noted that in the first and second embodiments, in the step a), the first oral digital data 14 can be alternatively acquired by obtaining a patient's oral bite mold, installing the jig 12 into the oral bite mold, and scanning the oral bite mold the jig 12 by an oral scanner.

In conclusion, the present invention can save the production time of the artificial tooth. By means of the present invention, the user can design the digital prosthesis 164 and generate the digital oral modes 20 and 28 after acquiring the first oral digital data 14; next, the user can process and prepare the solid prostheses 25 and 32 and the solid oral models 22 and 30. In this way, it is not necessary to prepare the dental bar or abutment as the prior art did before the dental crown or plate is prepared, thus indeed saving the production time.

Although the present invention has been described with respect to specific preferred embodiments thereof, it is in no way limited to the specifics of the illustrated structures but changes and modifications may be made within the scope of the appended claims.

What is claimed is:

1. A method of preparing a digital model and an artificial tooth applied to dental implant, comprising steps of:
    a) arranging a jig under a condition that there is a fixture in a patient's oral cavity, the fixture having a connection interface formed at a top side thereof, the jig having a feature and an abutting interface, the abutting interface being formed at a bottom side of the jig and corresponding to the connection interface, the feature being exposed outside the fixture and dental gum in the patient's oral cavity, the connection interface being combined with the abutting interface to enable the jig to be combined into the fixture; and scanning the patient's oral cavity by an oral scanner to acquire a first oral digital data and then saving it in a computer;
    b) operating the computer to select one of digital prostheses, each of which overlaps a digital jig having a digital feature corresponding to the feature of the jig, from a prosthetic database in the computer, combining the selected digital prosthesis and the first oral digital data by the overlap of the feature of the digital jig and that of the jig in the first oral digital data, and then removing the jig and the digital jig from the first oral digital data to generate a second oral data;
    c) generating a digital oral model based on the second oral digital data; and
    d) preparing a solid oral model based on the digital oral model, the digital prosthesis being substantialized to become a propositional prosthesis.

2. The method as defined in claim 1 further comprising a step e), after the step d), of preparing a solid prosthesis based on the digital prosthesis,
    the solid prosthesis having a joint interface corresponding to the connection interface of the fixture;
    creating a dental crown on the propositional prosthesis and then adjusting the dental crown according to the solid oral model; and
    finally installing the dental crown to the solid prosthesis to complete an artificial tooth.

3. The method as defined in claim 2, wherein the solid prosthesis is made of metal, ceramic, resin or wax, and then processed by a numerical processing machine or casted or both.

4. The method as defined in claim 1, wherein the digital prosthesis is a digital precise dental bar or a digital artificial abutment.

5. The method as defined in claim 1, wherein the prepositional prosthesis is made of metal, ceramic, resin, or wax and then processed by a numerical processing machine or casted or both.

6. The method as defined in claim 1, wherein the step a) further comprises sub-steps of acquiring an oral bite mold from the patient's oral cavity, then installing the jig to the oral bite mold, and finally scanning the oral bite mold instead of the patient's oral cavity by the oral scanner to acquire the first oral digital data.

7. The method as defined in claim 1, wherein the propositional prosthesis is independent from the solid oral model, the solid oral model having a cavity, the propositional prosthesis having a plug-in portion fitting the cavity to be fixedly inserted into the cavity without any movement.

8. A method of preparing an artificial tooth for dental implant, comprising steps of:
    a) arranging a jig under a condition that there is a fixture in a patient's oral cavity, the fixture having a connection interface formed at a top side thereof, the jig having a feature and an abutting interface, the abutting interface being formed at a bottom side of the jig and corresponding to the connection interface, the feature being exposed outside the fixture and dental gum in the patient's oral cavity, the connection interface being connected with the abutting interface to enable the jig to be combined into the fixture; and scanning the patient's oral cavity by an oral scanner to acquire a first oral digital data and saving it in a computer;
    b) operating the computer to select one of a digital prostheses, each of which overlaps a digital jig having a digital feature corresponding to the feature of the jig, from a prosthetic database in the computer, combining the selected digital prosthesis and the first oral digital data by the overlap of the feature of the digital jig and that of the jig in the first oral digital data, and then removing the jig and the digital jig from the first oral digital data and the digital prosthesis to generate a second oral data;
    c) separate the digital prosthesis from the second oral digital data to enable the digital prosthesis to expose the abutting interface and to enable the second oral digital data to expose the connection interface, and then generate a digital oral model based on the second oral digital data; and
    d) creating a solid oral model based on the digital oral model and a solid prosthesis based on the digital prosthesis, the digital prosthesis being substantialized to become a solid prosthesis, the solid prosthesis having a joint interface corresponding to the connection interface of the fixture.

9. The method as defined in claim 8, wherein the digital prosthesis in the step b) is a digital precise dental bar or a digital abutment.

10. The method as defined in claim 8, wherein the solid prosthesis is made of metal, ceramic, resin, or wax and then processed by a numerical processing machine or casted or both.

11. The method as defined in claim 8, wherein the step a) further comprises sub-steps of scanning the patient's oral cavity to acquire a third oral digital data and saving it in the computer before the jig is combined into the fixture, the oral digital data having the connection interface, whereby comparing the connection interface of the third oral digital data with that of the second oral digital data can confirm whether the second oral digital data is accurate or not.

12. The method as defined in claim 8, wherein the step a) further comprise sub-steps of acquiring an oral bite mold from the patient's oral cavity, then installing the jig to the oral bite mold, and finally scanning the oral bite mold instead of the patient's oral cavity by the oral scanner to acquire the first oral digital data.

13. The method as defined in claim 8 further comprising a step e), after the step d), of combining the solid prosthesis into the solid oral model by combination of the joint interface and the connection interface, then creating an artificial tooth on the solid prosthesis, and finally adjusting the artificial tooth according to the solid oral model.

14. The method as defined in claim 13, wherein the artificial tooth in the step e) is prepared by directly building up porcelain on the solid prosthesis.

15. The method as defined in claim 13, wherein the step e) further comprises a sub-step of preparing a coping and a crown on the solid prosthesis to complete a dental crown and then installing the dental crown to the solid prosthesis to complete the artificial tooth.

* * * * *